(12) United States Patent
Kosikowski et al.

(10) Patent No.: US 10,786,191 B2
(45) Date of Patent: Sep. 29, 2020

(54) SYSTEM AND METHOD FOR SUPPORTING OF NEUROLOGICAL STATE ASSESSMENT AND FOR SUPPORTING NEUROLOGICAL REHABILITATION, ESPECIALLY WITHIN COGNITIVE AND/OR SPEECH DYSFUNCTION

(71) Applicant: AssisTech Sp. z o.o, Gdańsk (PL)

(72) Inventors: Robert Kosikowski, Gdańsk (PL); Bartosz Kunka, Gdańsk (PL)

(73) Assignee: AssisTech Sp. z o.o., Gdansk (PL)

( * ) Notice: Subject to any disclaimer, the term of this patent is extended or adjusted under 35 U.S.C. 154(b) by 131 days.

(21) Appl. No.: 15/983,490

(22) Filed: May 18, 2018

(65) Prior Publication Data

US 2018/0296151 A1 Oct. 18, 2018

Related U.S. Application Data

(63) Continuation-in-part of application No. PCT/PL2016/000094, filed on Sep. 6, 2016.

(30) Foreign Application Priority Data

Nov. 18, 2015 (PL) .................................. P.414836

(51) Int. Cl.
*A61B 5/16* (2006.01)
*A61B 3/113* (2006.01)
(Continued)

(52) U.S. Cl.
CPC .............. *A61B 5/163* (2017.08); *A61B 3/113* (2013.01); *A61B 3/14* (2013.01); *A61B 5/0062* (2013.01); *A61B 5/486* (2013.01); *A61B 5/741* (2013.01); *A61B 5/7415* (2013.01); *A61B 5/7435* (2013.01); *A61B 5/7445* (2013.01); *A61M 21/00* (2013.01); *G06F 3/04883* (2013.01);
(Continued)

(58) Field of Classification Search
CPC ........... A61B 3/113; A61B 3/14; A61B 5/163; A61B 5/0062
See application file for complete search history.

(56) References Cited

U.S. PATENT DOCUMENTS

| | | | |
|---|---|---|---|
| 2014/0160434 A1* | 6/2014 | Brown, Jr. ............. | A61B 3/113 351/210 |
| 2014/0171756 A1* | 6/2014 | Waldorf ................ | A61B 3/032 600/301 |
| 2017/0173262 A1* | 6/2017 | Veltz ................... | A61M 5/1723 |

* cited by examiner

*Primary Examiner* — John J Lee
(74) *Attorney, Agent, or Firm* — Andrzej Malarz (57) ABSTRACT

The invention provides the supporting system for neurological state assessment and neurological rehabilitation, especially within cognitive and/or speech dysfunction, characterized in that, the processing unit (PU) is integrated with the screen (S), which is equipped with the touch input sensors (TIS), said camera and light sources work within infrared radiation, wherein the infrared camera (IFC) is integrated with at least two infrared light sources (ILS). The infrared light sources (ILS) and the infrared camera (IFC) are formed into a movable component (MC) in the way that the infrared light sources (ILS) are located symmetrically and uniaxially on both sides of the infrared camera (IFC) in the movable component (MC). The movable component (MC) is connected with the processing unit (PU) through the screen (S). In another aspect the invention provides the method for supporting of neurological state assessment and neurological rehabilitation, especially within cognitive and/or speech dysfunctions.

16 Claims, 6 Drawing Sheets (51) Int. Cl.
  *A61B 5/00* (2006.01)
  *A61B 3/14* (2006.01)
  *A61M 21/00* (2006.01)
  *G06F 3/0488* (2013.01)
  *G09B 19/04* (2006.01)
  *G10L 13/04* (2013.01)
  *H04N 5/225* (2006.01)
  *H04N 5/33* (2006.01)

(52) U.S. Cl.
  CPC ............ *G09B 19/04* (2013.01); *G10L 13/043* (2013.01); *H04N 5/2253* (2013.01); *H04N 5/2256* (2013.01); *H04N 5/33* (2013.01); *A61M 2021/005* (2013.01); *A61M 2021/0027* (2013.01); *A61M 2205/3303* (2013.01); *A61M 2205/3313* (2013.01); *A61M 2205/52* (2013.01)

SYSTEM AND METHOD FOR SUPPORTING OF NEUROLOGICAL STATE ASSESSMENT AND FOR SUPPORTING NEUROLOGICAL REHABILITATION, ESPECIALLY WITHIN COGNITIVE AND/OR SPEECH DYSFUNCTION

This patent application is a continuation-in-part application filed under 35 U.S.C. 111(a), claiming a priority of the PCT Application No. PCT/PL2016/000094, filed on Sep. 6, 2016, under 35 U.S.C. 365(c), and claiming a priority of the Polish Patent Application No. P.414836, filed on Nov. 18, 2015, the contents of which are incorporated in their entirety into the present continuation-in-part application by reference.

The present invention relates to the system and method for supporting of neurological state assessment and for supporting of neurological rehabilitation, especially dedicated for patients suffering for cognitive and/or speech dysfunction, that works based on gaze tracking and measuring of visual fixation point on the screen.

In order to perform the neurological state assessment and diagnosis, especially as far as the cognitive and/or the speech functions are concerned, the neurological screening methods, such as PET, MRI, fMRI, EEG are customary used.

The screening methods are limited available because of its expensiveness. The methods allow only stimulated cerebral parts to be examined. According to the literature data, such neurological examination provides neither sufficient nor objective information about the neurological patient's state of consciousness, especially as far as the cognitive and/or speech disorders are concerned (Sörös P: *The neural correlates of consciousness: electrophysiological and neuroimaging evidence for conscious processing in vegetative state*. Clinical Neurophysiology 2011, 122:641-642; Fellinger R, Klimesch W, Schnakers C, Perrin F, Freunberger R, Gruber W, Laureys S, Schabus M: *Cognitive processes in disorders of consciousness as revealed by EEG time-frequency analyses*. Clinical Neurophysiology 2011, 122:2177-2184; Cruse D, Chennu S, Chatelle C, Bekinschtein T, Fernández-Espejo D, Pickard J, Laureys S, Owen A M: *Bedside detection of awareness in the vegetative state: a cohort study*. Lancet 2011, 378:2088-2094; Laureys S, Goldman S, Phillips C, Van Bogaert P, Aerts J, Luxen A, Franck G, Maquet P: *Impaired effective cortical connectivity in vegetative state: preliminary investigation using PET*. NeuroImage 1999, 9:377-382).

There are some factors that determine the limitation of the known neurological screening methods effective using, especially when the patients with severe brain damage are examined.

Among the main factors there are:
  a) low availability of the specialistic apparatus
  b) the patient's discomfort or other medical disturbance while being located inside the MRI/fMRI/PET scanner
  c) impaired patient's feedback reaction caused by reduced capability to react properly to examiner's orders
  d) high costs generated by necessity to perform the examination repeatedly, in order to objectify the comprehensive diagnoses of patients.

There are other methods that provide support of neurological state assessment or neurological rehablititation, especially as far as the cognitive or speech disorders are concerned. The methods are based on the behavioral examination and the patient's neurological state is diagnosed with using of diagnostic scales, which are exampled by the following ones:

GCS (Glasgow Coma Scale), CRS-R (Coma Recovery Scale-Revised), FOUR (Full Outline of Unresponsiveness), SMART (Sensory Modality Assessment and Rehabilitation Technique), MMSE (Mini-Mental State Examination), NIHSS (The National Institutes of Health Stroke Scale).

These methods are based on patient's state of consciousness observation, so the patient is diagnosed through his responses and/or reactions to examiner's orders or stimulus, for example motor or auditory stimulus. These methods are the subjective type of the neurological state assessment.

The known methods cannot be effectively performed in numerous neurological disorders, for example amyotrophic lateral sclerosis, dysfunctions relate to inability to get the patient's reaction and/or response to either external stimulus or examiner's order, although patient's consciousness is preserved.

The majority of the methods that provide support of the neurological state assessment and neurological rehabilitation, especially within cognitive and/or speech dysfunctions, base on the subjective diagnosis of the patient's behavioral response and/or reaction. These methods do not provide objective information of the dysfunction and the neurological state of neurological patients especially with cognitive and/or speech dysfunctions. None of the known methods recommend or even suggest of using visual fixation point analyses.

Based on foregoing, there is therefore need to provide methods that enables to objectify the neurological state assessment and therefore enable to provide support for neurological examination and rehabilitation, the method which enable the patients to interact with stimuli even in the presence of severe neurological dysfunction.

The methods for visual fixation point tracking location on the computer screen are known from the publications and patents publication.

Polish patent application P.391974 and US2012/0026276 patent application disclose the method of the visual fixation point measuring location with the computer screen surface. The method bases on that the user's eye surface is illuminated and light reflection from the surface of pupil is analyzed with the assistance of monitoring camera. From the patent application P.391974 is known that light sources, preferably the infrared range, are installed in the axis of the camera and in the corners of the computer monitor and/or nearby. Then, depending on the user's eyes characteristics, the light sources are simultaneously or consecutively turned on and/or off. The constellations of reflections from the surface of the user's pupil are recorded by the camera. Then the record is analyzed by the computer and the software. The using of the method in teleconferencing, texts reading supporting and social communicating is also disclosed.

U.S. patent application Ser. No. 11/570,840 discloses the method of controlling computer with a user's sight playing role of computer's mouse. The particular graphical components displayed on the screen, that relate to computer mouse actions, allow to select the desired action by gaze, which is then performed on the indicated control icon. The process allows to select the control action, carried out with the mouse, by the gaze, and choose a place where the mouse action is to be performed. The method does not enable supporting neurological state assessment and neurological rehabilitation.

The visual fixation point or eye tracking analyses method is also used for developing an educational software and refers to doing exercises of visual attention while computer games are generated. The method does not allow to support the neurological patient's assessment especially with cognitive and/or speech dysfunctions.

The oculographic device is used for the visual fixation point location measuring analyses. The oculographic device is mainly used for marketing research conducting and for social communication but not for supporting of neurological state assessments and for neurological rehabilitation of severe patients especially with cognitive and/or speech disorders.

Based on foregoing, there is therefore need to objectify the neurological state analyses, diagnosis and ameliorate neurological rehabilitation and therefore to provide objective methods for supporting neurological state assessments and/or neurological rehabilitation in patients with neurological dysfunctions, especially within cognitive and/or speech disorders. This set the objective of the present invention.

The invention provide a solution to the problem by providing the supporting system for neurological state assessment and neurological rehabilitation, especially within cognitive and/or speech dysfunction, characterized in that, the processing unit PU is integrated with the screen S, which is equipped with the touch input sensors, said camera and light sources work within infrared radiation. The infrared camera is integrated with at least two infrared light sources, and the infrared light sources and the infrared camera are formed into a movable component in the way that the infrared light sources are located symmetrically and uniaxially on both sides of the infrared camera in the movable component, while the movable component is connected with the processing unit through the screen.

In the embodiment, the movable component has a movability within a range of the angle of elevation with regard to plane of the screen.

In the following embodiment, the movable component is located in the lower part of the screen.

In the following embodiment, the screen is attached to the movable extension arm.

In the second aspect of the invention, there is provided method for supporting of neurological state assessment and neurological rehabilitation, especially within cognitive and/or speech dysfunctions, characterized in that the method comprising the step of:
providing the processing unit equipped with the memory and integrated with the screen equipped with the touch input sensors wherein the infrared camera is integrated with at least two infrared light sources located symmetrically and uniaxially on both sides of the camera forming the movable component, and such movable component is connected with the screen;
implementing in the memory of processing unit the first algorithm and the second algorithm. The first algorithm, that performs the analyses of user's eyes movements images acquired from the infrared camera and that determines the user's visual fixation point on the screen, that is represented on the screen by the visual fixation indicator, while the second algorithm performs the analyses of the visual fixation indicator position on the screen and generates the feedback signal in the form of acoustic signals and/or graphical elements.

The next of the step of the method is dividing the area of the screen into at least two virtually separated areas of the active field of the screen. While the visual fixation point position is continuously determined by the processing unit within the first algorithm in the way of acquiring the user's eyes movements images by the infrared camera and simultaneously acquiring them by the processing unit, the defined graphical element is projected within at least one of the separated area of the active field of the screen, and preferably simultaneously the defined acoustic signal is emitted, preferably the speech sound. Based on the analyses of the visual fixation point, the visual fixation indicator is displayed on the screen and when the visual fixation indicator is sustained within the indicated separated area of the active field of the screen for longer than 0.5 secs, preferably 2-3 secs, the indicated separated area of the active field of the screen is activated by the second algorithm and simultaneously the feedback signal containing location of the activated separated area of the active field of the screen is generated by the processing unit and stored in its memory. The following step of the method is generating of the defined feedback graphical element and projecting it within at least one activated separated area of the active field of the screen and preferably simultaneously emitting the defined acoustic signal, preferably the speech sound. After that, preferably the manner is repeated from the step of dividing the area of the screen into at least two virtually separated areas of the active field of the screen, projecting following defined graphical element within the area of at least one separated area of the active field of the screen and preferably simultaneously emitting the defined acoustic signal, preferably the speech sound.

In the embodiment, at least one acoustic testing signal from the sound level range of (0%; 100%> is emitted and the volume level controlling, which is visualized by the graphical element of the volume level controlling, preferably text element, is projected within at least one separated area of the active field of the screen. When the visual fixation indicator is sustained within the area of the indicated separated area of the active field of the screen for longer than 0.5 sec, preferably 2-3 secs, the indicated separated area of the active field of the screen is activated by the second algorithm and simultaneously the feedback answer signal containing location of the activated separated area of the active field of the screen is generated by the processing unit and stored in its memory and. After that, preferably, the manner is repeated, wherein the following acoustic testing signals of progressively higher or lower sound level are emitted and the following feedback answer signals containing location of the activated separated area of the active field of the screen are analyzed by the processing unit. Based on the analyses, the optimal sound level range of the generated acoustic signals to be emitted is determined. The embodiment then allows to adjust the sound level of the defined acoustic signal to be emitted, to the determined optimal sound level range of the generated acoustic signals.

In the embodiment, the defined graphical testing element is projected within at least one separated area of the active field of the screen, and when the visual fixation indicator is sustained within the indicated separated area of the active field of the screen for longer than 0.1 sec, preferably 1 sec, the indicated separated area of the active field of the screen is activated by the second algorithm and simultaneously the first control signal is generated by the processing unit and stored in the memory. The first control signal contains XY coordinate of the activated separated area of the active field of the screen and the XY coordinate of the separated area of the active field of the screen that the defined graphical testing element was projected within. In the processing unit the analysis of compatibility of the XY coordinates acquired with the first control signal is performed by the second algorithm. When the XY coordinates are compatible, the first control signal of compatibility is generated by the processing unit and stored in the memory, and then the following defined graphical testing element is projected within the separated area of active field of the screen, which is differently located than previously. When the visual fixation indicator is sustained within the indicated separated area of active field of the screen for longer than 0.1 sec, preferably 1 sec, the indicated separated area of the active field of the screen is activated by the second algorithm and simultaneously the following control signal is generated by the processing unit and stored in the memory. The following control signal contains XY coordinate of the activated separated area of the active field of the screen and the XY coordinate of the subsequent separated area of the active field of the screen that the following defined graphical testing element was projected within. In the processing unit the analysis of compatibility of XY coordinates acquired with following control signals is performed by the second algorithm, and if the XY coordinates are compatible, the following control signal of compatibility is generated by the processing unit and stored in the memory. The manner of defined graphical testing element generation is repeated until the graphical testing elements are projected within each of virtually separated areas of the active fields of the screen. Based on the stored control signals of compatibility, the location of compatibility areas of the active field of the screen is indicated through XY coordinates of the indicated with visual fixation indicator and simultaneously activated area that defined graphical testing element was projected within. The embodiment then allows the defined graphical elements are projected within the compatibility areas of active field of the screen.

The invention enables to objectify the neurological state assessment and neurological rehabilitation, especially within cognitive and/or speech functions. The invention allows neurological patients, especially cognitive and/or speech disordered, to be more precisely examined, and the neurological rehabilitation to be more effectively performed. The system according to the invention makes the integrated device, that allows to be adjusted to work with the patients in serious neurological condition.

The invention enables through the visual fixation point position continuous tracking during the defined graphical elements projection and/or the acoustic signals emission to obtain the actual neurological state information, related to the pathophysiological basis of the disorder, that is not enabled to be obtained through the known methods.

The method according to the invention is based on the visual fixation point measuring on the screen and enables to adjust the examination performance to the specificity of patient's neurological condition. Patients therefore are able to interact with the visual and acoustic stimuli. The methods works in the causative way of sending particular signals and therefore patients can easily interact regardless of cognitive and/or speech disorders.

The invention enables to obtain the actual and objective information of the neurological profile of the subject's cognitive functions. The known methods enable merely to examine the cerebral system structure and do not provide information about the subject's degree of examiner's orders comprehension and make the objectivity of neurological state examination distinctly reduced. The known methods do not enable to determine if subject can perceive the objects before him/her consciously, if patient understands single words, sentences, if he/she differentiates shapes, colors, etc.

The following detailed description of the invention, which describes an exemplary embodiments of the invention, taken in conjunction with the accompanying drawings are presented. The schematic view of the supporting system for neurological state assessment and neurological rehabilitation as well as the user's optimal sound level range analysis and field of vision examination is presented in the FIG. 1; schematic view of the method for supporting of neurological state assessment is presented in the FIG. 2; the schematic view of the method for supporting of comfortable hearing range examination is presented in the FIG. 3; the schematic view of the method of the acoustic signals emission level adjusting to the comfortable hearing range of user is presented in the FIG. 4; the schematic view of the method of user's field of vision within the screen assessment is presented in the FIG. 5 and FIG. 6; the schematic view of the method of the defined graphical elements projected within the area of the screen adjusting, based on the examination of user's field of vision, is presented in FIG. 7.

EXAMPLE 1

The system and the method providing support of cognitive and speech functions assessment—the structure of the system.

Figure 1:
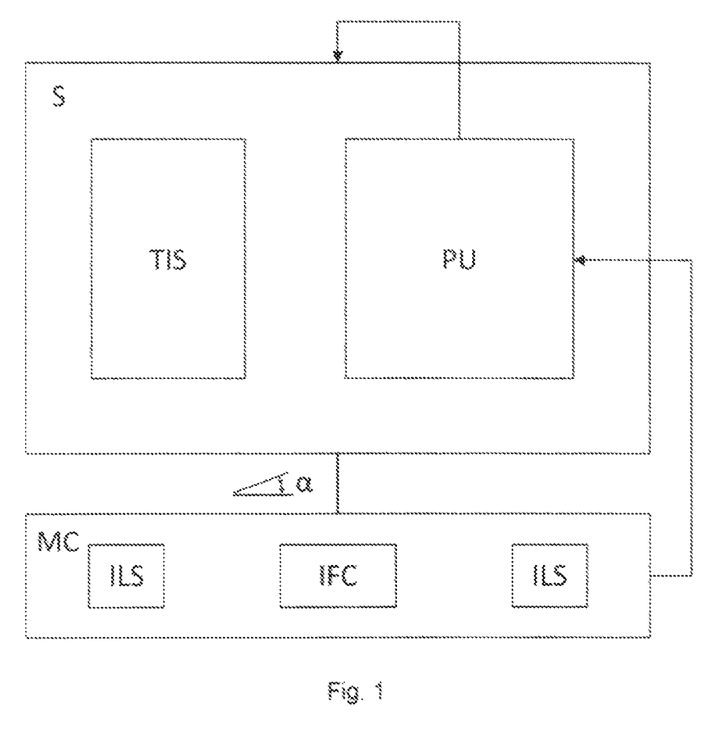

As presented in the FIG. 1, the system comprises the processing unit PU in the form of computer with the memory, which is the integrated with the screen S equipped with the touch input sensors TIS and the speakers.

The system is equipped with two infrared light sources ILS, that enable to indicate the visual fixation point position through generating infrared light reflections, that are reflected from the surface of user's cornea and acquired by the infrared sensitive camera IFC. The infrared light sources ILS are integrated with the infrared sensitive camera IFC in this way, that the infrared light sources ILS are located symmetrically and uniaxially on the both sides of the camera IFC and put together into the longitudinal cover to be formed into the movable component MC in the form of attachment. The movable component MC, which is connected with the processing unit PU through the screen S and located in the lower part of the screen S, is up and down tiltable in a range of 45 degrees of the angle of elevation $\alpha$ in relation to the perpendicular location of the movable component MC towards the screen S. The screen S with the movable component MC is attached to the movable extension arm EA in the form of movable stand.

The method providing support of neurological state examination of the user.

Figure 2:
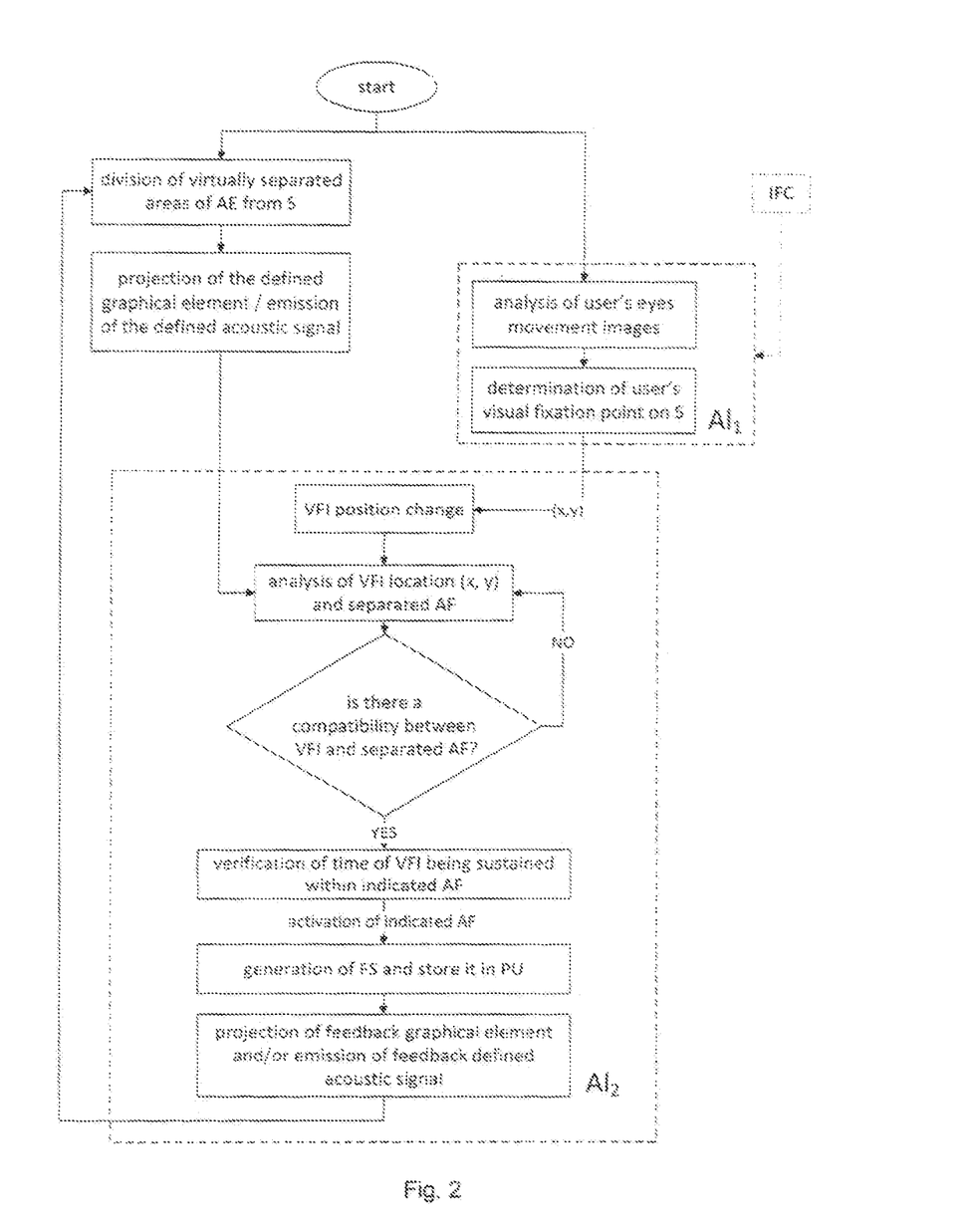

As presented in the FIG. 2, the first algorithm Al1 is implemented in the memory of the processing unit PU—the computer. The operations of the first algorithm Al1 are to perform the analyses of user's eyes movements images, which are acquired from the infrared camera IFC and that determines the user's visual fixation point position on the screen S, that is represented and visualized on the screen S by the visual fixation indicator VFI with the frequency of 30 Hz. The second algorithm Al2 is implemented in the memory of the processing unit PU—the computer. The operations of the second algorithm Al2 are to perform the analyses of the visual fixation indicator VFI position on the area of the active field AF of the screen S, and that generates feedback signal in the form of predefined acoustic signals and predefined graphical elements.

The area of the screen S is divided into four virtually separated areas of the active field AF of the screen S. The manner is predefined before starting the examination or exercise during rehabilitation and depends on type of examination of the patients. and difficulty level of the test case of performed exercise.

The four predefined separated areas of the active field AF of the screen S are virtually separated from the area of the screen S. The separated areas of the active fields AF of the screen S are located contiguously in the horizontal line of the plane of the screen S, wherein each separated area of the active field AF of the screen S is a square in shape and the length of the square side is equal to 40% of the height of the screen S. The centre of area framing set of four separated area of the active field AF of the screen S is concurrent with the centre of the screen S.

The cognitive and speech disordered neurological patient to be examined is located before the screen S. The location of the screen S attached to the movable extension arm EA is adjusted to the patient through the adjusting movements of the movable extension arm EA in this way, that the patient is located 60 cm before the screen S and the movable component MC, located in the lower part of the screen S, is to be positioned parallelly to the patient's interpupillary line, so that the patient's eyes are situated in the angle of view of the infrared camera IFC.

Then the defined graphical elements in pictogram form are projected simultaneously within the four virtually separated areas of the active field AF of the screen S, wherein one of the defined graphical element is the previously defined "correct graphical element" and simultaneously the defined acoustic signal in a form of the speech sound is emitted from the speakers, wherein the emitted defined acoustic signal is the exercise order, and the solution of the exercise is to choose the previously defined "correct graphical element", which is projected within one of the four virtually separated areas of the active field AF of the screen S. There are ten such exercises to be generated.

The method works in the way that during the assessment the user's eyes movements images are continuously being acquired from the infrared camera IFC and simultaneously acquired by the processing unit PU in order to being analyzed by the first algorithm AL1 in order to determine the visual fixation point position and then, based on the analyses of the visual fixation point of the user, the visual fixation indicator VFI is displayed on the screen S by the second algorithm Al2. The visual fixation point position is continuously being indicated, wherein the system works with two different modes of the visual fixation point assessment: the passive mode and the active mode. The passive mode of the visual fixation point indicating works in this way, that although the visual fixation indicator VFI is sustained within the area of the indicated active field AF of the screen S for at least 2 secs, the area of the indicated separated active field AF of the screen is not being activated by the second algorithm Al2 and simultaneously the feedback signal FS containing location of the indicated separated area of the active field AF of the screen S is neither acquired by the processing unit PU nor stored in memory. This mode is used in case of patients with serious neurological disorders who require more time for processing and understanding of content displayed in the separated area of the active field AF of the screen S. The active mode of the visual fixation point indicating works in this way, that when the visual fixation indicator VFI is sustained within the area of the indicated separated active field AF of the screen S for at least 2 secs, the area of the indicated separated active field AF of the screen S is activated by the second algorithm Al2 which is visualized in the way, that the activated area of the indicated separated area of the active field AF of the screen S is distinguished from the entire area of the active field AF of the screen S with a thick red colored frame and simultaneously the feedback signal containing location of the activated separated area of the active field AF of the screen S is generated by the processing unit PU and stored in its memory with information in a binary format, where "0" corresponds to an incorrect answer and describes the situation when VFI is sustained at least 2 secs in the indicated separated area of the active field AF of the screen S with previously defined "wrong graphical element"; "1" corresponds to a correct answer and describes the situation when VFI is sustained longer than 2 secs in the area of the indicated separated active field AF of the screen S with previously defined correct answer, which is when the previously defined graphical element, which is projected within the area of the one of the separated area of the active field AF of the screen S, is the defined "correct graphical element".

The activated separated area of the active field AF of the screen S is set apart from the entire area of the screen S with a thick red colored frame when the feedback signal FS containing location of the activated separated area of the active field AF of the screen S is stored in the memory of processing unit PU with incorrect or correct answer, respectively signal "0" and "1" as indicated above.

The visual fixation point position is continuously being determined and when the visual fixation indicator VFI is sustained within the virtually previously divided one separated area of the active field AF of the screen S for at least 2 secs, the area of indicated separated area of the active field AF of the screen S is activated by the second algorithm Al2 what is visualized in this way, that the activated separated area of the active field AF of the screen S is distinguished from the entire area of the screen S with a thick red colored frame and simultaneously the first feedback signal $FS_1$ containing the location of the activated separated area of the active field AF of the screen S is generated by the processing unit PU and stored in the memory with information in a binary format, where "0" corresponds to an incorrect answer and "1" corresponds to a correct answer, what was explained before.

Depending on the first generated feedback signal $FS_1$, the previously indicated defined feedback graphical element in a form of a pictogram, is generated and projected within the activated separated area of the active field AF of the screen S and simultaneously the previously defined feedback acoustic signal in a form of acoustic signal is emitted, by which the activated separated area of the active field AF of the screen S is confirmed.

Then the following previously defined graphical elements in pictogram form are projected within the four areas of the active field AF of the screen S, wherein one of the following defined graphical elements is the following "correct graphical element" and simultaneously the following previously defined acoustic signal in a form of the speech sound is emitted from the speakers. The emitted acoustic signal is the subsequent exercise order, and the solution of the subsequent exercise is to choose the following previously defined "correct graphical element" which is projected within one of the virtually separated four areas of the active field AF of the screen S. As described above, then visual fixation indicator VFI is sustained within indicated separated area of the active field AF of the screen S longer that 2 secs, the indicated separated area of the active field AF of the screen S is activated, and therefore the second feedback signal $FS_2$ is generated and the defined feedback graphical element is projected.

Then the manner is being repeated from the step of dividing the area of the screen S into virtually separated areas of the active field AF of the screen S. The number of separated areas of the active field AF depends on type and difficulty level of the current test case of performed examination until the examinations are concluded. Depending of single words understanding during examination, the number of the separated area of the active field AF of the screen S changes from 2 (for normal difficulty level) to higher numbers (for the highest difficulty level).

The method enables precisely and objectively to examine the user's cognitive and speech functions through the appraisal of patient's level of maintained capability of single words meaning understanding. The information about cognitive and speech function is obtained through the analyses of the generated and stored feedback signals $FS_{1-n}$ containing locations of the activated separated areas of the active field AF of the screen S. The analyses of the feedback signals $FS1-_n$ enable to appraise the headway of neurological rehabilitation.

The supporting method provides therefore objectivity of neurological disorders examination and therefore allow to perform neurological rehabilitation.

EXAMPLE 2

The method of comfortable hearing range assessment.

In the example, the optimal sound level range of the generated acoustic signals means that the sound level range is adjusted to be comfortably heard by the individual examined patient.

The system is constructed as described in the example 1.

Figure 3:
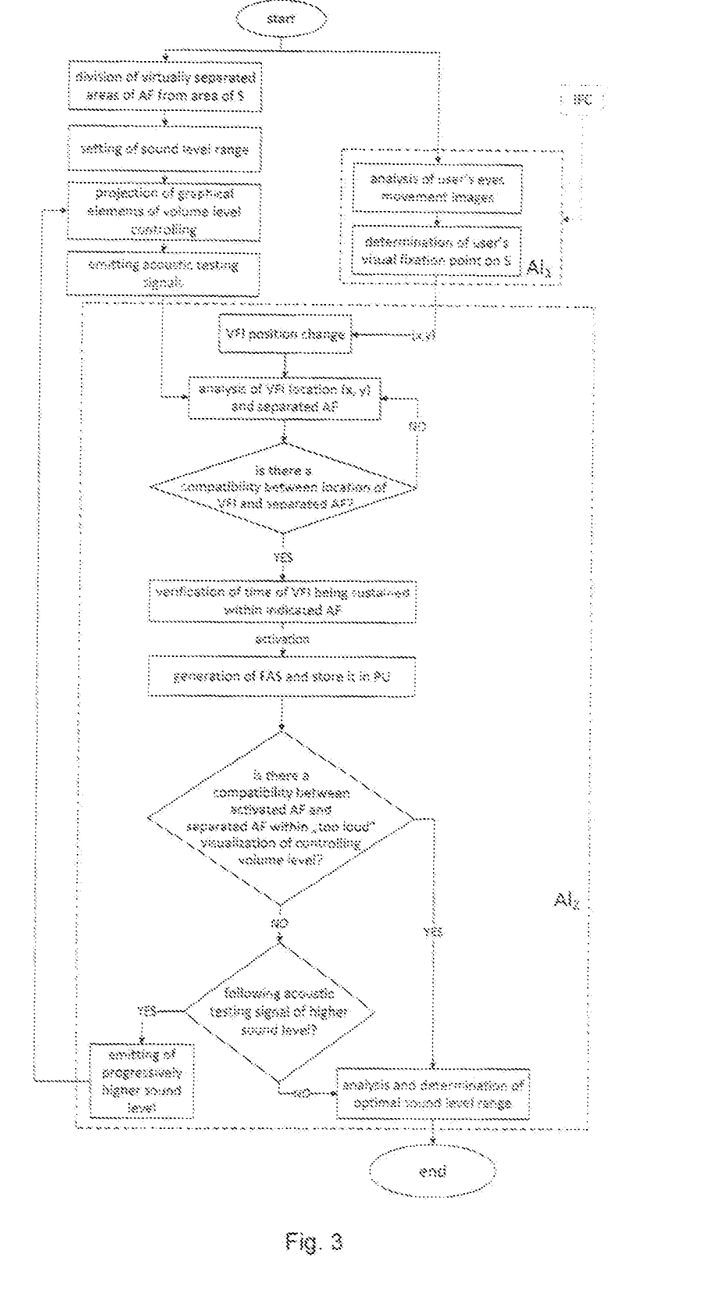

The user's comfortable hearing range assessment is performed as presented in the FIG. 3. Before the defined graphical elements are projected within the separated areas of the active field AF of the screen S the initial sound level is to be set down. The acoustic testing signals to be emitted are the speech sounds, which are understandable for the user. There are three areas of the active field AF of the screen S, that are virtually separated from the area of the screen S. The separated areas of the active field AF of the screen S are located contiguously in the horizontal line of the plane of the screen S. The previously defined graphical elements of the volume level controlling are the pictograms projected within each of three separated areas of the active field AF of the screen S, wherein the defined graphical elements of volume level controlling are the text elements, containing the following answers options:

"Too quiet"
"Good"
"Too loud"

During the method, the user's eyes movements images are continuously being acquired from the infrared camera IFC and simultaneously acquired by the processing unit PU in order to being analyzed by the first algorithm AL1 in order to determine the visual fixation point position and then, based on the analyses of the visual fixation point, the visual fixation indicator VFI is displayed on the screen S by the second algorithm Al2. The visual fixation point position is continuously being indicated.

Then the first acoustic testing signal at 10% of maximal sound level is emitted from the speakers and the graphical elements of the volume level controlling are projected. When the visual fixation indicator VFI is sustained within the area of the indicated separated area of the active field AF of the screen for at least 2 secs, the indicated separated area of the active field AF of the screen S is activated by the second algorithm AL2 what is visualized in this way, that the virtually activated separated area of the active field AF of the screen S distinguished from the entire area of the screen S with a thick red colored frame and simultaneously the first feedback answer signal $FAS_1$ containing location of the activated separated area of the active field AF of the screen S is generated by the processing unit PU and stored in the memory. The first feedback answer signal $FAS_1$ provides information of the graphical element of volume level controlling that is indicated through the visual fixation point indicator VFI and when the indicated option of answer is "Too loud", then the examination is terminated, and the optimal sound level range of the generated acoustic signals to be emitted is indicated. If not, the following acoustic testing signals are to be emitted until the activated separated area of the active field AF of the screen S corresponds to the volume level controlling of "too loud" loud" or the acoustic testing signal is emitted at a maximum available sound level of the device.

When the acoustic testing signals emission is concluded, the generated feedback answer signals $FAS_{1-n}$ are analyzed by the processing unit PU, and then, based on the analyses, the optimal sound level range of the generated acoustic signals to be emitted during the assessment or rehabilitation method is enabled to be adjusted. The feedback answer signals $FAS_{1-n}$ are illustrated with discreet XY chart, wherein the etiquettes corresponding to the graphical elements of volume level controlling are depicted on the horizontal axis of the graph and the values of emitted sound level are depicted on the vertical axis of the graph with percentage scale.

As the medical research bring evidence, the patients with craniocerebral injuries are auditory oversensitive. That determines the importance to perform the comfortable hearing level examination according to the invention (J. Landon, D. Shepherd, S. Stuart, A. Theadom, S. Freundlich, *Hearing every footstep: Noise sensitivity in individuals following traumatic brain injury*, Neuropsychological Rehabilitation, 22, 3, 391-407, 2012).

EXAMPLE 3

The method of the defined acoustic signals level emission adjusting to the optimal sound level range.

The system is constructed as described in the example 1.

Figure 4:
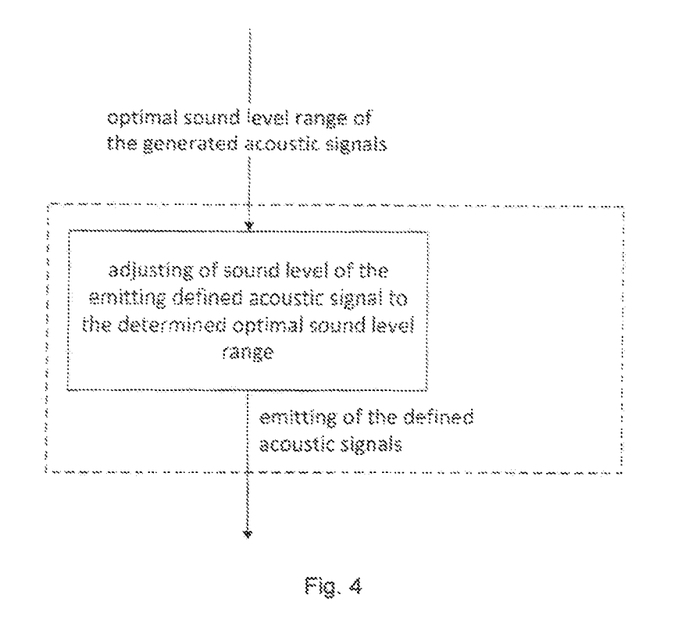

As presented in the FIG. 4 the optimization of acoustic signals range emission to the comfortable hearing range is based on the results of the comfortable hearing range examination as described in the example 2—optimal sound level range of the generated acoustic signals.

The method for supporting of neurological state assessment and neurological rehabilitation is performed as described in the example 1, wherein the defined acoustic signals are emitted within the sound level of the determined before optimal sound level range. Hence the sound level of defined acoustic signals to be emitted is adjusted to user's perceptive capacity, and the method, according to the invention, to provide support of neurological state examination and neurological rehabilitation, regarding to the user with hearing system disorders, especially with oversensitive hearing, is enabled to be effectively used.

EXAMPLE 4

The method of user's range of vision assessment.
The system is constructed as described in the example 1.
The method is performed as described in the example 1.
In order to individualize the support of neurological state examination, the assessment of range of eyes' vision is performed, as presented in the FIG. 5, before the defined graphical elements are projected within the separated areas of the active field AF of the screen S.

Figure 5:
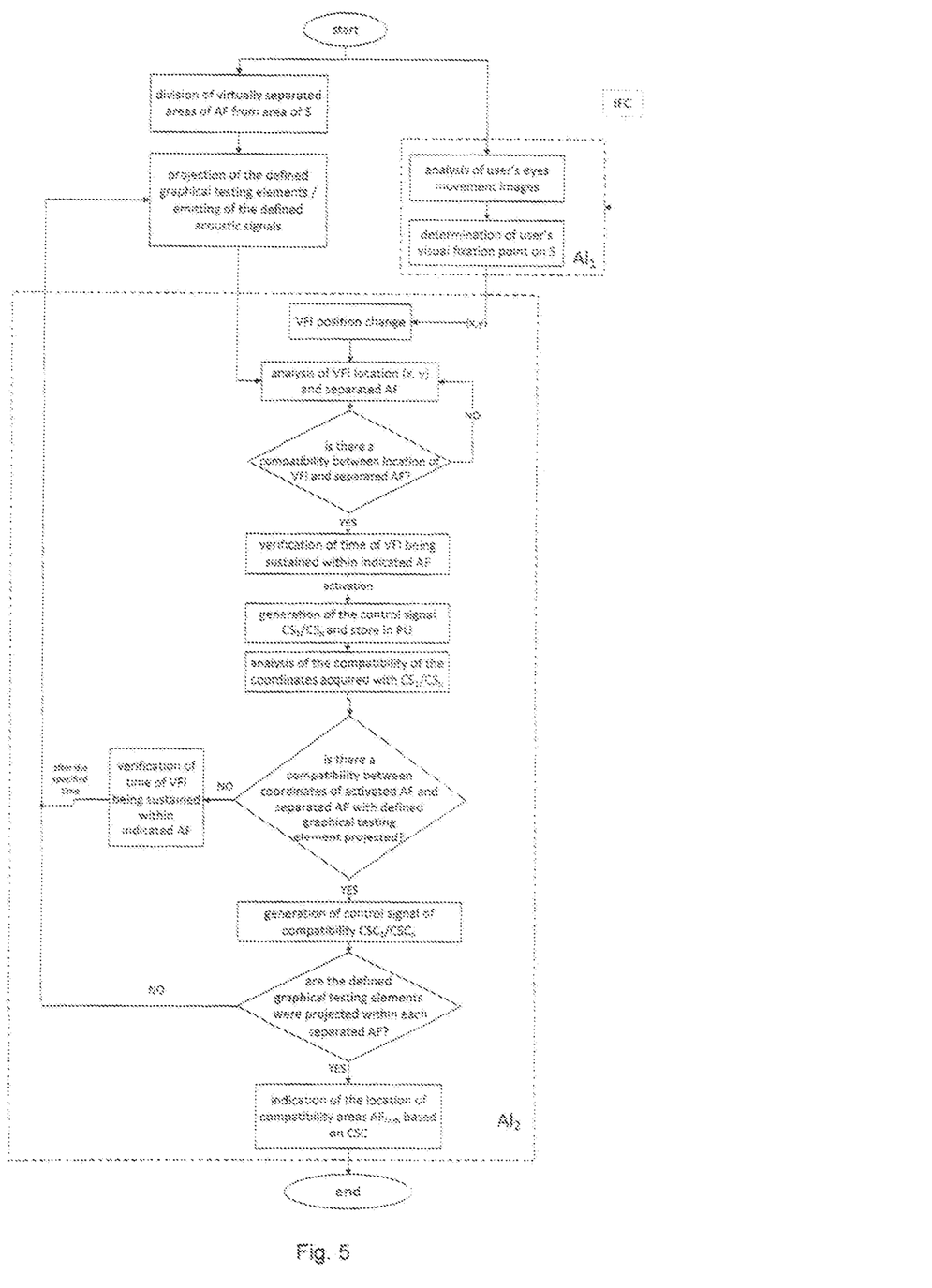

The method is performed through visual fixation point indication with defined graphical testing elements, which are projected within the separated areas of the testing active field AF of the screen S, wherein the separated areas of the testing active field AF of the screen S are separated from the entire area of the screen S.

The entire area of the screen S is divided into 15 equal separated areas of the testing active field AF of the screen S, split into 3 rows and 5 columns. The defined graphical testing element is a pictogram depicting a turned off light bulb, which is projected within the separated area of the testing active field AF of the screen S, wherein the pictogram of the turned off light bulb does not fill the entire separated area of the testing active field AF of the screen S, which is projected within, but is projected in the central part of the area of the testing active field AF of the screen S.

The defined graphical testing element is projected within the first separated area of the testing active field AF of the screen S, which is located in the upper left corner of the area of the screen S. Then, the location of the user's visual fixation point ion the screen S are determined by the first algorithm Al1 and when the visual fixation indicator VFI is sustained within the indicated area of the previously defined separated area of the testing active field AF of the screen S for at least 0.6 secs, the indicated separated area of the testing active field AF of the screen S is activated by the second algorithm Al2 and simultaneously the first control signal $CS_1$ containing XY coordinate of the activated separated area of the testing active field AF of the screen S and the XY coordinate of the separated area of the testing active field AF of the screen S, that the defined graphical testing element was projected within are generated by the processing unit PU and stored in the memory. Then, by the second algorithm Al2, the processing unit PU activates the analysis of compatibility of the generated in the first control signal $CS_1$ XY coordinates of the areas of the testing active filed AF of the screen S and when the coordinates compatibility analysis is positive which means the coordinates are compatible, then the first control signal of compatibility $CSC_1$ is generated by the processing unit PU and stored in its memory. The compatibility occurrence and generation of signal of compatibility $CSC_1$ is visualized in this way, that the projected within the activated separated area of the testing active field AF of the screen pictogram depicting the turned off light bulb is replaced with the pictogram depicting the turned on light bulb.

Then the following defined graphical testing element is projected within the separated area of the defined testing active field AF of the screen S wherein the separated area of the testing active field AF of the screen S is differently located than previously and when the visual fixation indicator VFI is sustained within the area of the subsequent indicated separated testing active field AF of the screen S for longer than 0.6 secs, the subsequent indicated separated area of the testing active field AF of the screen S is activated by the second algorithm Al2 and simultaneously the following—second control signal $CS_2$ contains XY coordinate of the subsequent activated separated area of the indicated testing active field AF of the screen S and the XY coordinate of the subsequent separated area of the testing active field AF of the screen S that the following graphical testing element was projected within, are generated by the processing unit PU and stored in the memory. Then, by the second algorithm Al2, the processing unit PU activates the analysis of compatibility of the generated following—second control signal $CS_2$—the compatibility of the XY coordinates and when the coordinates compatibility analysis is positive then the following—second control signal of compatibility $CSC_2$ is generated by the processing unit PU and stored in the memory.

The manner of defined testing graphical element generation is being recurred until the graphical testing elements are projected within each of 15 areas of the separated areas of the testing active field AF of the screen S, wherein the following defined graphical testing elements are projected in the order from left to right within a row, beginning from the top row, through the medium row and ending with the bottom row of the divided area of the field of screen S. Based on the generated and stored control signals of compatibility $CSC_{1-15}$, the method enables to diagnose the user's range of vision through the determination of location of the compatibility areas of the active field $AF_{com}$ of the screen S which means the areas of the testing active field AF of the screen S where the defined graphical testing elements were projected and indicated with the visual fixation indicator VFI and therefore activated.

When it is evinced through the assessment that, the mostly right located column of the areas of the testing active field AF of the screen S is beyond the user's range of vision then the following control signals of compatibility are generated: $CSC_{1-4}$, $CSC_{6-9}$, $CSC_{11-14}$. The virtually separated areas of the testing active field AF of the screen S located on the right part of the screen S that were not indicated with the visual fixation point VFI that would be characterized by control signals of compatibility with lower indexes of 5, 10, 15 and that were not generated.

When the range of vision assessment is concluded, the generated control signals of compatibility $CSC_{1-15}$ are visualized in this way, that the areas of the testing active field AF of the screen S that the generated control signals of compatibility $CSC_n$ refer to, are visualized as filled with green color virtually separated areas, wherein the areas of the testing active field AF of the screen S, that the generated control signals of compatibility $CSC_n$ do not refer to, are visualized as filled with red color virtually separated areas.

The field range of vision assessment, according to the invented method, enables to diagnose either the user's range of vision is normal or defected. As far as the patients with brain damage are concerned, the visual field defects are commonly evinced, for example hemianopias.

Figure 6:
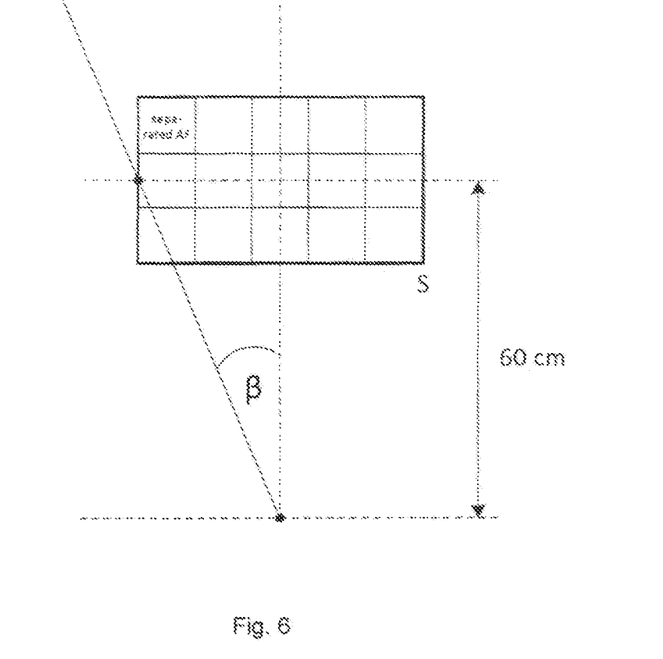

The range of vision assessment, according to the invented method, enables not only to examine the user's range of vision that refers to the area of the screen, but also the user's range of vision in general that is characterized through the value of the β angle that can be calculated and the calculation is based on the distance between the subject and the screen and width of perceived part of screen (range of vision). The method is thoroughly presented in the FIG. 6.

EXAMPLE 5

The method to adjust the location of the defined graphical elements projected within the area of the screen The system is constructed as described in the example 1.

Figure 7:
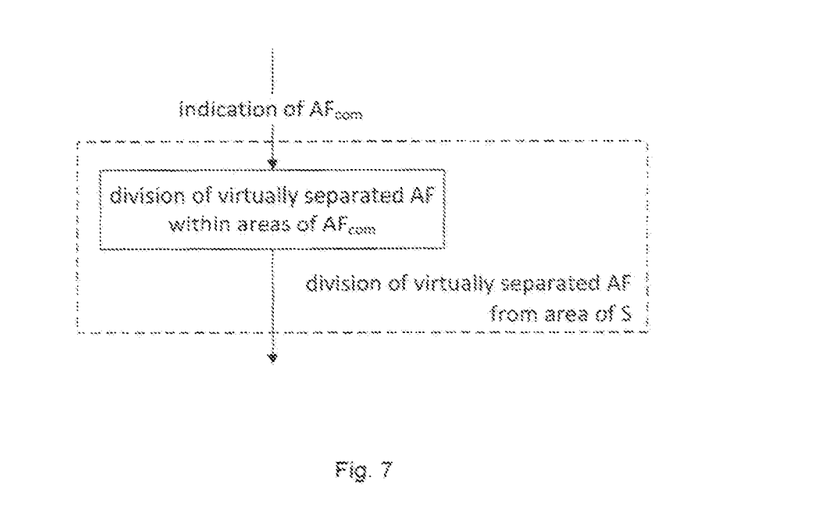

Based on the results, obtained through the range of vision assessment, as described in the example 4, it is enabled to adjust the area of the active field AF of the screen S, that the defined graphical elements are to be projected within, as is presented in the FIG. 7. The separated areas of the active field AF of the screen S, are to be virtually separated from the compatibility areas of the active field $AF_{com}$, defined as the areas of the testing active field AF of the screen to be indicated through the visual fixation indicator VFI and that the defined graphical testing element were projected within.

For example, when it is evinced through the range of vision assessment that the user is incapable to see the 20% of the right side of the screen S area, then, during the neurological rehabilitation and the neurological state examination performing, the defined graphical elements are to be projected within the remaining 80% of the area of the screen S, virtually separated into areas of the active field AF of the screen S.

Hence the defined graphical elements projection is adjusted to the user's perceptional capabilities and it is enabled to perform the method according to the invention with the user of the range of view defected.

The invention claimed is:

1. A supporting system for neurological state assessment and neurological rehabilitation, especially within cognitive and speech dysfunction, comprising a processing unit with memory, a screen, light sources for eye illumination and a camera, wherein the processing unit (PU) is integrated with the screen (S) and said camera and light sources work within infrared radiation, wherein the infrared camera (IFC) is integrated with at least two infrared light sources (ILS) characterized in that the infrared light sources (ILS) and the infrared camera (IFC) are formed into a movable component (MC) in the way that the infrared light sources (ILS) are located symmetrically and uniaxially on both sides of the infrared camera (IFC) in the movable component (MC), which is located in the lower part of the screen (S), while the movable component (MC) has a movability within a range of the angle of elevation (α) with regard to plane of the screen (S) and is connected with the processing unit (PU) through the screen (S), which is equipped with the touch input sensors (TIS).

2. The system according to claim 1, wherein the screen (S) is attached to a movable extension arm (EA).

3. A method for supporting of neurological state assessment and neurological rehabilitation, especially within cognitive and speech dysfunctions based on the visual fixation point tracking on the screen by the system for measuring visual fixation point equipped with a camera and light sources, said method comprising the steps of:
providing the processing unit (PU) equipped with the memory and integrated with the screen (S) equipped with the touch input sensors wherein the infrared camera (IFC) is integrated with at least two infrared light sources (ILS) located symmetrically and uniaxially on both sides of the camera (IFC) forming the movable component (MC), and such movable component (MC) is connected with the screen (S);
implementing in the memory of processing unit (PU): the first algorithm (AI1) that performs the analyses of user's eyes movements images acquired from the infrared camera (IFC) and that determines the user's visual fixation point on the screen (S) that is represented on the screen (S) by the visual fixation indicator (VFI);
implementing the second algorithm (AI2) that performs the analyses of the visual fixation indicator (VFI) position on the screen (S) and generates the feedback signal in the form of acoustic signals and/or graphical elements;
dividing the area of the screen (S) into at least two virtually separated areas of the active field of the screen (AF);
projecting the defined graphical element within at least one of the separated area of the active field of the screen (AF), while the visual fixation point position is continuously determined by the processing unit (PU) within the first algorithm (AI1) in the way of acquiring the user's eyes movements images by the infrared camera (IFC) and
acquiring simultaneously them by the processing unit (PU);
displaying the visual fixation indicator (VFI) on the screen (S), based on the analyses of the visual fixation point;
activating the indicated separated area of the active field (AF) of the screen (S) by the second algorithm (AI2) when the visual fixation indicator (VFI) is sustained within the indicated separated area of the active field (AF) of the screen (S) for longer than 0.5 secs;
generating simultaneously the feedback signal (FS) containing location of the activated separated area of the active field (AF) of the screen (S) by the processing unit (PU) and stored in its memory;
generating the defined feedback graphical element; and
projecting the defined feedback graphical element within at least one activated separated area of the active field (AF) of the screen (S).

4. The method according to claim 3, further comprising the step of emitting simultaneously a defined acoustic signal when the defined feedback graphical element is generated and projected within at least activated separated area of the active field (AF) of the screen (S).

5. The method according to claim 3, further comprising the step of emitting simultaneously speech sound when the defined feedback graphical element is generated and projected within at least activated separated area of the active field (AF) of the screen (S).

6. The method according to claim 3, further comprising the step of activating the indicated separated area of the active field (AF) of the screen (S) by the second algorithm (AI2) when the visual fixation indicator (VFI) is sustained within the indicated separated area of the active field (AF) of the screen for 2-3 secs.

7. The method according to claim 3, further comprising the step of emitting simultaneously the defined acoustic signal when the defined feedback graphical element is generated and projected within at least activated separated area of the active field (AF) of the screen (S).

8. The method according to claim 3, further comprising the step of emitting simultaneously speech sound when the defined feedback graphical element is generated and projected within at least activated separated area of the active field (AF) of the screen (S).

9. The method according to claim 3, said method comprising the steps of:
emitting at least one acoustic testing signal from the sound level range of more than 0%, to 100% inclusive
projecting the volume level controlling, which is visualized by the graphical element of the volume level controlling within at least one separated area of the active field (AF) of the screen (S), wherein the graphical element of the volume level controlling is text element;
activating the indicated separated area of the active field (AF) of the screen (S) by the second algorithm (AI2), when the visual fixation indicator (VFI) is sustained within the area of the indicated separated area of the active field (AF) of the screen (S) for longer than 0.5 sec;
generating simultaneously the feedback answer signal (FAS) containing location of the activated separated area of the active field (AF) of the screen (S) by the processing unit (PU) and stored in its memory;
repeating the manner;
emitting the following acoustic testing signals of progressively higher or lower sound level;
analyzing the following feedback answer signals ($FAS_n$) containing location of the activated separated area of the active field (AF) of the screen (S) by the processing unit (PU); and
determining based on the analysis, the optimal sound level range of the generated acoustic signals to be emitted.

10. The method according to the claim 9, wherein the sound level of the defined acoustic signal to be emitted is adjusted to the determined optimal sound level range of the generated acoustic signals.

11. The method according to claim 9, wherein the graphical element of the volume level controlling is a text element.

12. The method according to claim 9, further comprising the step of activating the indicated separated area of the active field (AF) of the screen (S) by the second algorithm (Al2) when the visual fixation indicator (VFI) is sustained within the indicated separated area of the active field (AF) of the screen for 2-3 secs.

13. The method according to claim 9, further comprising the step of adjusting the sound level of the defined acoustic signal to be emitted to the determined optimal sound level range of the generated acoustic signals.

14. The method according to claim 3, said method comprising the steps of:
projecting the defined graphical testing element within at least one separated area of the active field (AF) of the screen (S);
activating the indicated separated area of the active field (AF) of the screen (S) by the second algorithm (Al2) when the visual fixation indicator (VFI) is sustained within the indicated separated area of the active field (AF) of the screen (S) for longer than 0.1 sec;
generating simultaneously the first control signal ($CS_1$) by the processing unit (PU); and
storing in the memory, wherein the first control signal ($CS_1$) contains XY coordinate of the activated separated area of the active field (AF) of the screen (S) and the XY coordinate of the separated area of the active field (AF) of the screen (S) that the defined graphical testing element was projected within;
performing by the second algorithm (Al2), in the processing unit (PU), the analysis of compatibility of the XY coordinates acquired with the first control signal ($CS_1$);
generating the first control signal of compatibility ($CSC_1$) by the processing unit (PU), when the XY coordinates are compatible;
storing in the memory;
projecting then the following defined graphical testing element within the separated area of active field (AF) of the screen (S), which is differently located than previously;
sustaining the visual fixation indicator (VFI) within the indicated separated area of active field (AF) of the screen (S) for longer than 0.1 sec;
activating the indicated separated area of the active field (AF) of the screen (S) by the second algorithm (Al2);
generating simultaneously the following control signal ($CS_n$) by the processing unit (PU);
storing in the memory, wherein the following control signal ($CS_n$) contains XY coordinate of the activated separated area of the active field (AF) of the screen (S) and the XY coordinate of the subsequent separated area of the active field (AF) of the screen (S) that the following defined graphical testing element was projected within;
performing, by the second algorithm (Al2), the analysis of compatibility of XY coordinates acquired with following control signals ($CS_n$) in the processing unit (PU);
generating, by the processing unit (PU), if the XY coordinates are compatible, the following control signal of compatibility ($CSC_n$); and
storing in the memory;
repeating the manner of defined graphical testing element generation until the graphical testing elements are projected within each of virtually separated areas of the active fields (AF) of the screen (S); and
indicating the location of compatibility areas of the active field ($AF_{com}$) of the screen (S), through XY coordinates of the indicated with visual fixation indicator (VFI), based on the stored control signals of compatibility ($CSC_n$), and simultaneously activated area that defined graphical testing element was projected within.

15. The method according to claim 14, further comprising the step of activating of the indicated separated area of the active field (AF) of the screen (S) by the second algorithm (Al2) when the visual fixation indicator (VFI) is sustained within the indicated separated area of the active field (AF) of the screen (S) for 1 sec.

16. The method according to claim 14, further comprising the step of projecting the defined graphical elements within the compatibility areas of active field ($AF_{com}$) of the screen (S).

* * * * *